US010987025B2

(12) United States Patent
Vartiovaara et al.

(10) Patent No.: US 10,987,025 B2
(45) Date of Patent: Apr. 27, 2021

(54) SYSTEMS AND METHODS FOR A RESPIRATORY SENSOR

(71) Applicant: General Electric Company, Schenectady, NY (US)

(72) Inventors: Ville Vartiovaara, Helsinki (FI); Otto Valtteri Pekander, Helsinki (FI)

(73) Assignee: General Electric Company, Schenectady, NY (US)

( * ) Notice: Subject to any disclaimer, the term of this patent is extended or adjusted under 35 U.S.C. 154(b) by 625 days.

(21) Appl. No.: 15/385,259

(22) Filed: Dec. 20, 2016

(65) Prior Publication Data
US 2018/0168483 A1    Jun. 21, 2018

(51) Int. Cl.
*A61B 5/08* (2006.01)
*A61B 5/087* (2006.01)
*A61B 5/00* (2006.01)

(52) U.S. Cl.
CPC .......... *A61B 5/0878* (2013.01); *A61B 5/0028* (2013.01); *A61B 5/0803* (2013.01); *A61B 5/6819* (2013.01); *A61B 5/7228* (2013.01); *A61B 5/742* (2013.01); *A61B 5/7475* (2013.01)

(58) Field of Classification Search
CPC ... A61B 5/0878; A61B 5/7228; A61B 5/0028; A61B 5/6819; A61B 5/0803; A61B 5/742; A61B 5/7475
See application file for complete search history.

(56) References Cited

U.S. PATENT DOCUMENTS

| 5,914,701 | A | 6/1999 | Gersheneld et al. | |
|---|---|---|---|---|
| 6,777,992 | B2 | 8/2004 | Ziesler et al. | |
| 6,864,780 | B2 | 3/2005 | Doi et al. | |
| 6,992,565 | B1 | 1/2006 | Giesler | |
| 8,633,809 | B2 * | 1/2014 | Schenk | H04B 13/005 340/286.01 |
| 8,740,808 | B2 * | 6/2014 | Curti | A61B 5/087 600/537 |
| 2009/0112115 | A1 * | 4/2009 | Huang | A61B 5/083 600/532 |
| 2010/0179389 | A1 * | 7/2010 | Moroney, III | A61B 5/682 600/301 |
| 2012/0138801 | A1 * | 6/2012 | Vanderpohl | A61B 5/7278 250/349 |

(Continued)

FOREIGN PATENT DOCUMENTS

| WO | 2016065180 A1 | 4/2016 | |
|---|---|---|---|
| WO | WO-2016065180 A1 * | 4/2016 | ............. G01N 27/12 |

OTHER PUBLICATIONS

International Search Report and Written Opinion for PCT/US2017/066402, dated Apr. 26, 2018, 12 pages.

(Continued)

*Primary Examiner* — Navin Natnithithadha
*Assistant Examiner* — Andrey Shostak
(74) *Attorney, Agent, or Firm* — The Small Patent Law Group LLC; Dean D. Small

(57) ABSTRACT

Systems and methods are provided for a respiratory sensor for a medical monitoring system that does not require an internal power source. The systems and methods adjust an electrical characteristic of a respiratory sensor based on a property of interest of an airflow path, receiving an excitation signal, and generating a response based on the excitation signal and the electrical characteristic.

17 Claims, 8 Drawing Sheets

(56) References Cited

U.S. PATENT DOCUMENTS

2015/0123679 A1* 5/2015 Kuyvenhoven .... G06K 19/0717
324/652
2016/0338624 A1* 11/2016 Min .................... A61B 5/1473

OTHER PUBLICATIONS

Lorenzo et al., "Modulated Frequency Selective Surfaces for Wearable RFID and Sensor Applications," IEEE Transactions on Antennas and Propagation, IEEE Service Center, vol. 64, No. 10, Oct. 2016, 10 pages.

Corbishley et al., "Breathing Detection: Towards a Miniaturized, Wearable, Battery-Operated Monitoring System," IEEE Transactions on Biomedical Engineering, IEEE Service Center, vol. 55, No. 1, Jan. 2008, 10 pages.

Corroy et al.,; A Body-Coupled Communication and Radio Frequency Dual Technology Cooperation Protocol for Body-Area Networks; Institute for Theoretical Information Technology; 2010; 5 pages.

* cited by examiner

SYSTEMS AND METHODS FOR A RESPIRATORY SENSOR

BACKGROUND

The subject matter herein relates generally to systems and methods for a respiratory sensor for a medical monitoring system that does not require an internal power source.

When a patient is admitted into a healthcare facility, the patient is often connected to a plurality of sensors in contact with the patient, such as wearable sensors, cardiac sensor, breathing or respiratory sensor, and/or the like. The respiratory sensor is configured to detect a respiratory rate (e.g., breathing rate) of the patient, which is monitored by a clinician. The conventional respiratory sensor may be bands positioned around a rib cage and abdomen of a patient having sinusoid coils. The respiratory rate is determined based on changes in impedance of the sinusoid coils based on movement by the patient while breathing. However, the conventional respiratory sensors are noisy and susceptible to motion artifacts based on movement not related to breathing of the patient.

BRIEF DESCRIPTION

In an embodiment, a system (e.g., a respiratory monitoring system) is provided. The system includes a respiratory sensor positioned within an airflow path of a patient. The respiratory sensor has an electrical characteristic that varies based on a property of interest of the airflow path. The system further includes a transmission circuit communicatively coupled to the respiratory sensor. The transmission circuit is configured to transmit an excitation signal to the respiratory sensor. The respiratory sensor is configured to generate a response based on the excitation signal and the electrical characteristic.

In an embodiment, a method (e.g., for respiratory monitoring of a patient) is provided. The method includes adjusting an electrical characteristic of a respiratory sensor based on a property of interest of the airflow path, receiving an excitation signal, and generating a response based on the excitation signal and the electrical characteristic.

In an embodiment, a system (e.g., a respiratory monitoring system) is provided. The system includes a respiratory sensor positioned within an airflow path of a patient and in contact with a body of the patient. The respiratory sensor has an electrical characteristic that varies based on a property of interest of the airflow path. The system further includes a transmission circuit communicatively coupled to the respiratory sensor using a communication channel within the body. The transmission circuit is configured to transmit an excitation signal to the respiratory sensor. The respiratory sensor is configured to generate a response based on the excitation signal and the electrical characteristic. The system also includes a controller circuit operably coupled to the transmission circuit. The controller circuit is configured to determine at least one of a temperature or flow rate of the airflow path based on the electrical characteristic.

DETAILED DESCRIPTION

Figure 1:
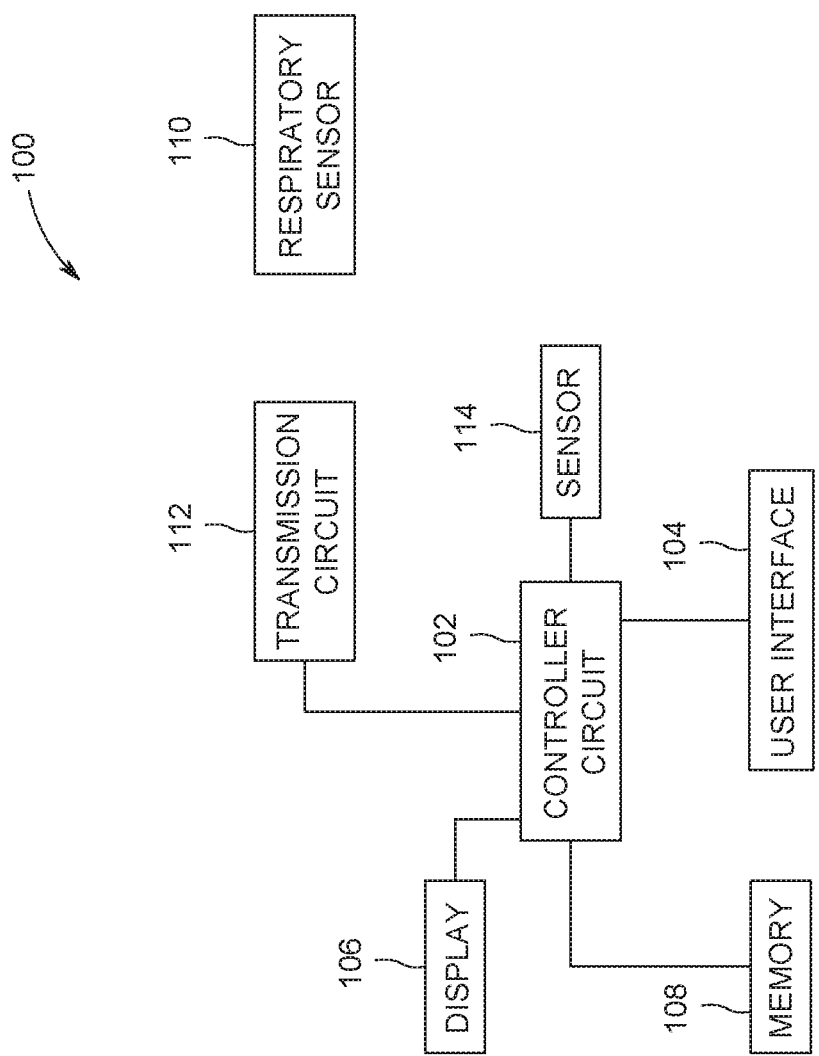
FIG. 1 is a block diagram of an embodiment of a medical monitoring system.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments described herein include systems and methods for a respiratory sensor for a medical monitoring system that does not require an internal power source. The respiratory sensor is positioned within an airflow of the nose and without a separate battery for the respiration sensor. The medical monitoring system is formed by separate transceivers, the respiratory sensor and a transmission circuit, which will provide a wireless or on body excitation signal and a sensor part that will reflect that signal back. The electrical characteristics (e.g., frequency, amplitude) of the excitation signal is received by the respiratory sensor and may be adjusted as a reflected signal modulated at proportional to an airflow of gas or change in temperature.

Optionally, the respiratory sensor may be communicatively coupled to the transmission circuit utilizing on/in body transceiver configured to transmit the excitation signal and listen for the reflected signal from the respirator sensor. Additionally or alternatively, the transmission circuit may be external from the body and located, for example, in the hub or hospital infrastructure. The respiratory sensor of the nose may be modulated by the excitation signal utilizing radio frequency (RF) or acoustic (for example Sonar pulses).

The respiratory sensor may include, for example, a resonator loop (e.g., inductor, metal spiral), and a capacitor. Additionally or alternatively, the resonator loop may be configured to be attached to the respiratory sensor to the patient. The one or more electrical characteristics of the capacitor (e.g., based on the temperature coefficients) are adjusted based on the ambient temperature of the respiratory sensor. The respiratory sensor receives the excitation pulse and is configured to generate a response based on the excitation pulse and the electrical characteristics of the respiratory sensor. For example, the electrical characteristics of the capacitor adjusts the resonance frequency of the respiratory sensor, which in turn modifies and/or adjusts the received excitation pulse that is reflected to the transmission circuit having a different frequency. Additionally or alternatively, the respiratory sensor may include a resistor. The one or more electrical characteristics of the resistor (e.g., based on the temperature coefficients) adjust, based on the ambient temperature, an amplitude of the excited signal of the generated response by the respiratory sensor.

A technical effect of the various embodiments allows an extremely small respiratory sensor to the nose without the need of cable or power.

FIG. 1 is a block diagram of an embodiment of a medical monitoring system (MMS) 100. The MMS 100 may include a transmission circuit 112 and a respiratory sensor 110. In connection with FIGS. 2A-B, the respiratory sensor 110 is positioned within an airflow path of a patient. It may be noted that the respiratory sensor 110 may be positioned in alternative positions relative to the nose 208 and/or the nostrils 204, 206 to be within the airflow path of the patient. The airflow path may represent a path on the body where ambient air is directed inwards and/or away from the body of the patient corresponding to the respiratory action of the patient.

Figure 2A:
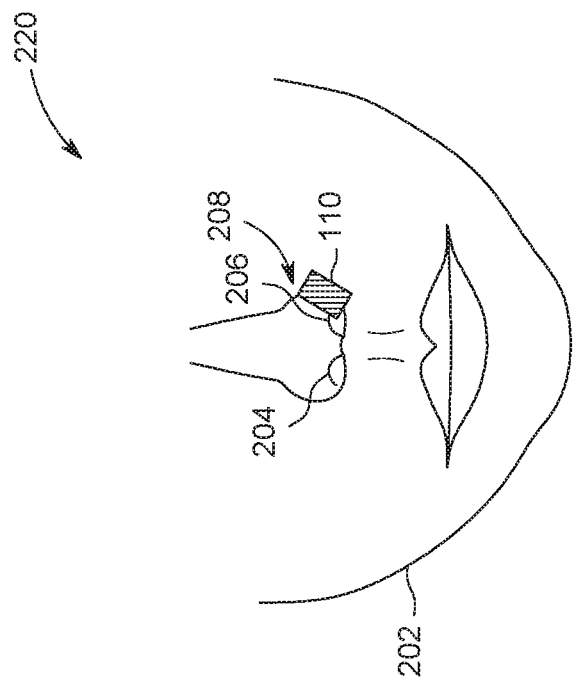
FIGS. 2A-B are positions of various embodiments of a respiratory sensor with respect to a patient.
Figure 2B:
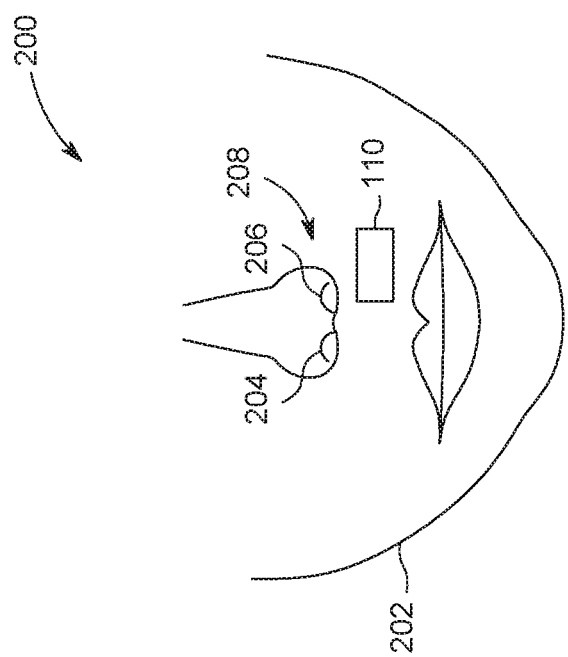
Figure 3A:
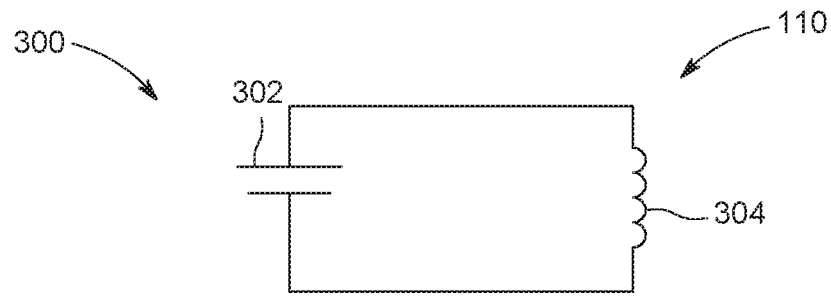
FIGS. 3A-D are schematic diagrams of various embodiments of a respiratory sensor.
Figure 3B:
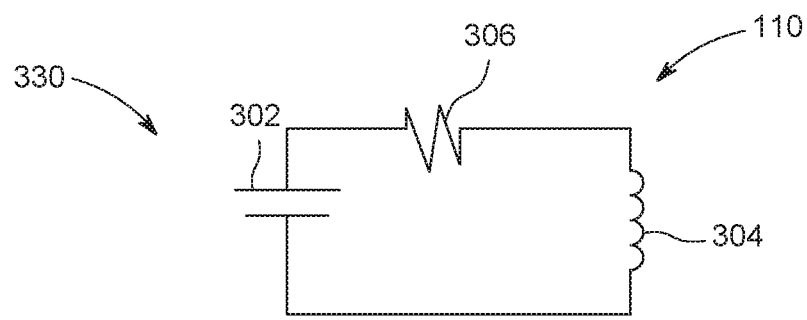
Figure 3C:
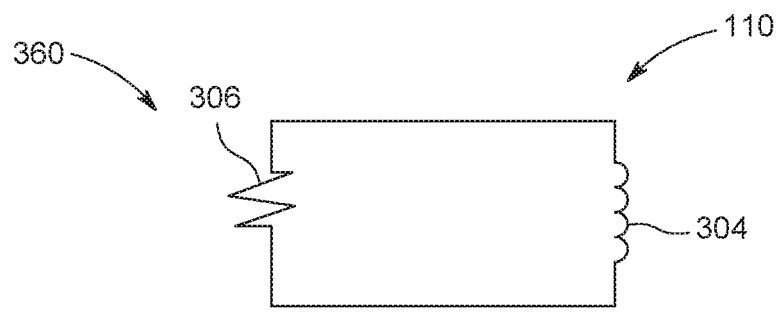
Figure 3D:
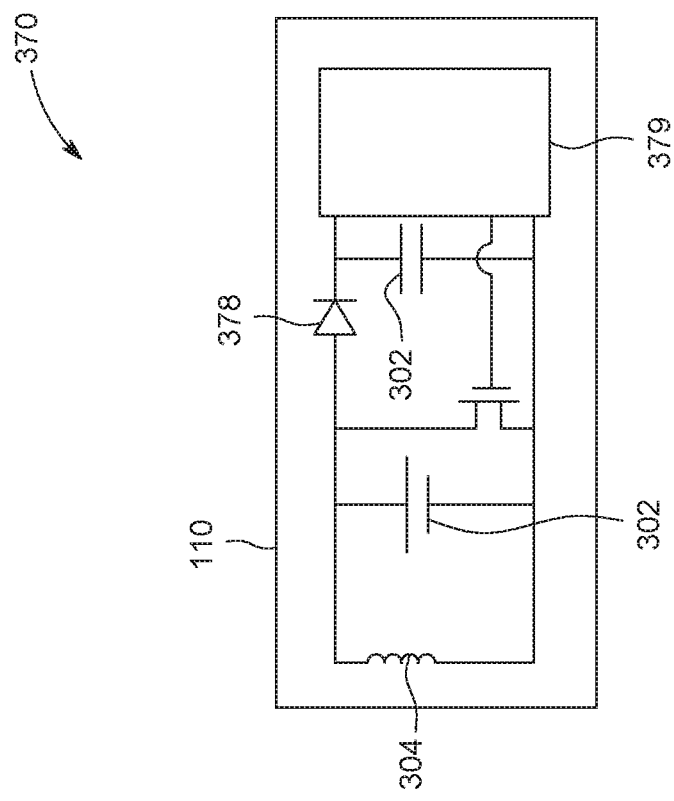
Figure 3D:
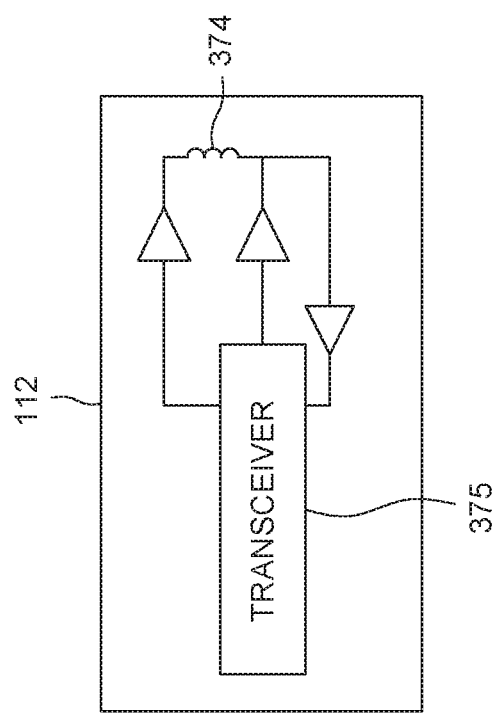

FIGS. 2A-B illustrate positions 200, 220 of various embodiments of the respiratory sensor 110 with respect to a patient 202. The positions 200, 220 of the respiratory sensor 110 are shown having the respiratory sensor 110 within the airflow path of the patient 202. For example, the airflow path may be aligned and/or proximate to the nostrils 204, 206 of a nose 208 of the patient 202. During respiratory action by the patient, ambient air is inhaled through the nostrils 204, 206 and subsequently exhaled through the nostrils 204, 206. FIG. 2A illustrates the respiratory sensor 110 positioned below one of the nostrils 206. As ambient air is inhaled and/or exhaled through the nostrils 206, the respiratory sensor 110 is exposed to the flow of the ambient air traversing the nostril 206.

FIG. 2B illustrates the respiratory sensor 110 coupled to one of the nostrils 206. For example, the respiratory sensor 110 may include a coil (e.g., inductor) configured to mechanically couple the respiratory sensor 110 to the nostril 206. As ambient air is inhaled and/or exhaled through the nostrils 206, the respiratory sensor 110 is exposed to the flow of the ambient air traversing the nostril 206.

Returning to FIG. 1, the transmission circuit 112 may be configured to be communicatively coupled to the respiratory sensor 110, such that the transmission circuit 112 can generate an excitation signal and receive a response from the respiratory sensor 110.

For example, the transmission circuit 112 may be configured to transmit an excitation signal and/or receive the response generated by the respiratory sensor 110 utilizing body-coupled communication (BBC). For example, the transmission circuit 112 may represent a capacitor having each terminal of the capacitor in contact with the body. Sometimes this body-coupled communication is referred to as "near-field intra-body communication". The BBC communication is described in U.S. Pat. Nos. 6,992,565, 6,777, 992, 6,223,018, 5,914,701, and 8,633,809, which are incorporated herein by reference in their entireties. The BCC enables the transmission circuit 112 and the respirator sensor 110 to exchange information through capacitive or galvanic coupling. The transmission circuit 112 may be configured to utilize the body of the patient as a communication channel. For example, the transmission circuit 112 and the respiratory sensor 110 are in contact with the body of the patient. The transmission circuit 112 may generate an electric field on a surface of the body corresponding to the excitation signal. The transmission circuit 122 is capacitively or galvanicly coupled to the respiratory sensor 110. The excitation signal is transmitted by modulating electric fields and either capacitively or galvanicly coupling tiny currents (e.g., pico amperes) into the body. The body conducts the tiny current to the respiratory sensor 110.

Additionally or alternatively, the transmission circuit 112 may include an RF circuit (not shown) configured to transmit the excitation signal to the respiratory sensor 110. The RF circuit may include a transmitter, a receiver, a transmitter and a receiver (e.g., a transceiver), and/or the like. Optionally, the RF circuit may be configured to receive information using the NFC protocol. The NFC protocol may be a short range wireless communication protocol defined in ISO/IEC 18092/ECMA-340, ISO/IEC 21481/ECMA-352, ISO/IEC 14443, and/or the like. For example, the transmission circuit 112 is configured to generate a magnetic field via the RF circuit, representing the excitation signal. The transmission circuit 112 may be positioned proximate to the respirator sensor 110 such that an RF circuit of the respiratory sensor 110 is positioned within the magnetic field. For example, the RF circuit may include an antenna (e.g., inductor, coil) configured to generate a current when positioned within the magnetic field of the transmission circuit 112. The current generated by the RF circuit may supply power to the other components of the respiratory sensor 110. As the RF circuit of the respiratory sensor 110 is within the magnetic field of the transmission circuit 112, the transmission circuit 112 and the respiratory sensor 110 are communicatively coupled with each other.

The MMS 100 may include a controller circuit 102 and a memory 108. The controller circuit 102 is communicatively coupled to the memory 108 and the transmission circuit 110. The controller circuit 102 may include and/or represent one or more hardware circuits or circuitry that include, are connected with, or that both include and are connected with one or more processors, controllers, and/or other hardware logic-based devices. Additionally or alternatively, the controller circuit 102 may execute one or more programmed instructions stored on a tangible and non-transitory computer readable medium (e.g., memory 108) to perform one or more operations as described herein.

The controller circuit 102 may be configured to generate the excitation signal, which is transmitted by the transmission circuit 110. For example, the excitation signal may represent a sinusoidal and/or digital signal having a set of predetermined electrical characteristics. The predetermined electrical characteristics may represent an amplitude, frequency, and/or the like of the excitation pulse.

The controller circuit 102 may receive the response generated by the respiratory sensor 110 via the transmission circuit 112. The controller circuit 102 may be configured to identify a difference between the excitation pulse and the response. For example, the response represents a modified and/or adjusted excitation pulse reflected and/or generated by the respiratory sensor 110 based on electrical characteristics of the respirator sensor 110 representative of a property of interest (e.g., temperature, flow rate, and/or the like) of the airflow path. Based on the changes in frequency, amplitude, and/or the like between the excitation pulse and the response, the controller circuit 102 may be configured to determine at least one of the temperature, flow rate of the airflow path, and/or the like based on the electrical characteristic of the response.

For example, based on the components (e.g., inductor, capacitor, resistor) of the respiratory sensor 110, as shown in FIGS. 3A-D, and the changes in electrical characteristics of the response relative to the excitation signal the controller circuit 102 may determine the property of interest.

FIGS. 3A-D are schematic diagrams 300, 330, 360, 370 of various embodiments of the respiratory sensor 110. For example, each schematic diagram 300, 330, 360, 370 may include at least one of a capacitor 302, an inductor 304, and/or a resistor 306.

The schematic diagram 300 illustrates the respiratory sensor 110 having the capacitor 302 and the inductor 304. The capacitor 302 may be configured to be a communication circuit of the respiratory sensor 110. For example, the capacitor 302 may be capacitively coupled to the transmission circuit 112 to form a communication channel within the body 202 of the patient. Additionally or alternatively, the inductor 304 may be configured as an RF circuit. For example, the inductor 304 may be configured to receive the excitation signal corresponding to a magnetic field generated by the transmission circuit 112.

Additionally or alternatively, the electrical characteristics of the capacitor 302 is affected by the ambient temperature. For example, the capacitance of the capacitor 302 may be based on a temperature coefficient (e.g., temperature coefficient of capacitance) of the capacitor 302. Changes in ambient temperature of the capacitor 302 relative to a reference temperature adjust the capacitance defined by the temperature coefficient. The ambient temperature of the capacitor 302 is adjusted based on the respiratory actions of the patient. For example, when the air of the airflow path is exhaled through the nostrils 204, 206, the air has a temperature approximately the same as the body temperature of the patient. Based on the higher temperature of the air in the airflow path, a temperature of the respiratory sensor 110 having the capacitor 302 is increased, which adjusts the electrical characteristics of the respiratory sensor 110. When the respiratory sensor 110 generates the response, the response corresponds to the excitation pulse modified by the electrical characteristics of the respiratory sensor 110.

For example, the temperature coefficient may be ±100 parts per million (ppm) having a reference temperature of 25 degrees Celsius. As the patient exhales, the temperature of the capacitor 302 increases to approximately 36 degrees Celsius (e.g., temperature change of 11 degrees Celsius), which shifts the capacitance of the capacitor 302 based on the temperature coefficient. For example, the capacitor 302 may have an inductance of 2 pF based on the temperature change of 11 degrees and the temperature coefficient of ±1000 ppm the capacitance of the capacitor 302 may be adjusted by ±0.022 pF (e.g., 2.022 pF, 1.978 pF). The adjustment in the capacitance of the capacitor 302 adjusts the resonance frequency of the respiratory sensor 110 based on the inductor 304 and the capacitor 302. The resonance frequency of the respiratory sensor 110 may represent a frequency adjustment to the excitation pulse modified by the electrical characteristics (e.g., change in capacitance) based on the property of interest (e.g., temperature) of the airflow path. For example, the inductor 304 may have an inductance of 0.2 pH such that, at the reference temperature of 25 degrees Celsius, the resonance frequency of the respiratory sensor 110 may be approximately 7.96 MHz. Based on the ambient temperature increasing to 36 degrees Celsius, the resonance frequency of the respiratory sensor 110 may be at approximately 7.91 MHz or 8 MHz.

The schematic diagram 370 illustrates the respiratory sensor 110 communicatively coupled to the transmission circuit 112 utilizing a modulated digital signal. The modulated digital signal may be transmitted using an RF field (e.g., traversing in the air) via inductors 304 and 374 as shown in the schematic diagram 370. Optionally, the modulated digital signal may be based on an NFC protocol such as ISO/IEC 18092/ECMA-340, ISO/IEC 21481/ECMA-352, ISO/IEC 14443, and/or the like. It may be noted that the modulated digital signal may be transmitted using the BBC via capacitively coupling between the transmission circuit 112 and the respiratory sensor 110.

The transmission circuit 112 is illustrated having a transceiver 375 conductively coupled to the inductor 374. The transceiver 375 with the inductor 374 is configured to generate the modulated digital signal representing the excitation signal via a magnetic field generated by the inductor 374. The modulated digital signal is received by the respiratory sensor 110 via the inductor 304. Based on the modulated digital signal, electrical power (e.g., current) is generated by the inductor 304 and is received by a diode 378. Based on the current generated by the inductor 304, a voltage potential is provided by the diode 378 activating a controller 379. The controller 379 may be embodied in hardware, such as a processor, application specific integrated circuit, or other logic-based device, that performs functions or operations based on one or more sets of instructions (e.g., software). The instructions on which the hardware operates may be stored on a tangible and non-transitory (e.g., not a transient signal) computer readable storage medium (e.g., memory). Alternatively, one or more of the sets of instructions that direct operations of the hardware may be hard-wired into the logic of the hardware. The controller 379 may be configured to generate a modulated digital signal representing a response based on the excitation signal received from the transmission circuit 112 and the electrical characteristics of the respiratory sensor 110.

Figure 4:
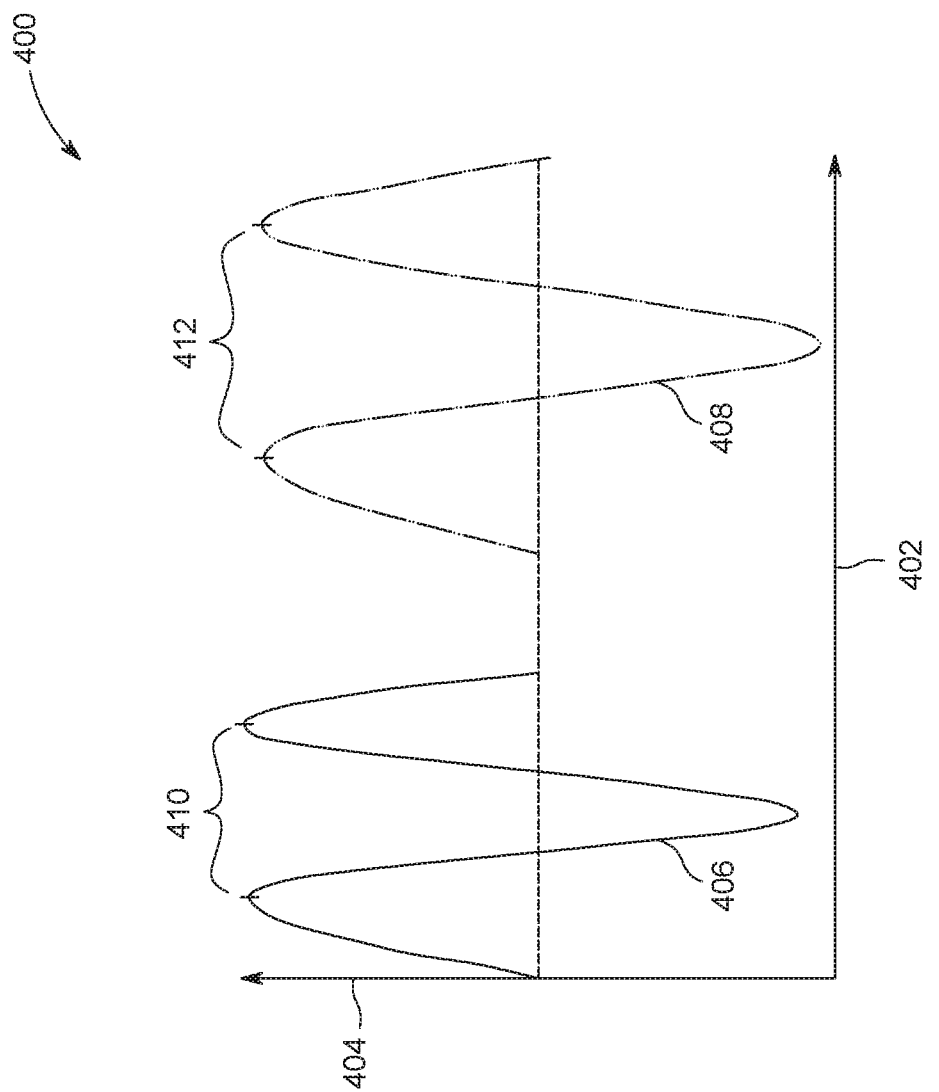
FIG. 4 is a graphical illustration of an excitation signal and a response, in accordance with an embodiment.

In connection with FIG. 4, the controller circuit 102 is configured to identify a difference between an excitation signal 406 and a response 408 to determine at least one of the temperature or flow rate based on the difference. For example, the electrical characteristics of the respiratory sensor 1110 represent an adjusted frequency of the excitation signal 406

FIG. 4 is a graphical illustration 400 of the excitation signal 406 and the response 408, in accordance with an embodiment. The excitation signal 406 and the response 408 are shown along a horizontal axis 402 representing time. A vertical axis 404 may represent an amplitude (e.g., voltage, current). For example, the excitation signal 406 is configured by the controller circuit 102 and transmitted by the transmission circuit 112. The excitation signal 406 is shown as a sinusoidal waveform in the graphical illustration 400, however, in various embodiments the excitation signal 406 may be a digital and/or binary signal. The excitation signal 406 may have a set of predetermined electrical characteristics. For example, the controller circuit 102 may configure the excitation signal 406 to have a frequency of 10 MHz and to have a period 410. It may be noted that the excitation signal 406 may have a different frequency than 10 MHz such as greater than 1 MHz (e.g., 100 MHz, 400 MHz, 1 GHz). The transmission circuit 112 receives the response 408 generated by the respiratory sensor 110. The response 408 represents a modified reflection of the excitation signal 406 based on the electrical characteristics of the respiratory sensor 110, such as the capacitor 302. The controller circuit 102 is configured to analyze the response 408 to determine at least one of the temperature or flow rate of the airflow path based on the temperature coefficient of the capacitor 302. For example, the controller circuit 102 may determine a frequency of the response based on a period 412 of the response 408. Based on the period 412, the controller circuit 102 may calculate the frequency of the response 408 to be 8 MHz. The controller circuit 102 may compare the frequency of the excitation signal 406 and the response 408 to determine the difference, such as 2 MHz. Based on the 8 MHz frequency of the response 408, the controller circuit 102 may determine a temperature of the respiratory sensor 110.

For example, the memory 108 may store the electrical characteristics of the inductor 304 (e.g., 2 pH) and the capacitor 302 (e.g., 2 pF), and the temperature coefficients (e.g., ±1000 ppm of the capacitor 302). Based on the frequency of 8 MHz, the controller circuit 102 may determine the capacitance of the capacitor 302 to be approximately 1.978 pF. The controller circuit 102 utilizing the adjusted capacitance may determine the temperature based on the temperature coefficient to be 36 degrees Celsius, representing a temperature of the airflow path.

Returning to FIG. 3B, the schematic diagram 330 illustrates the respiratory sensor 110 having the capacitor 302, the inductor 304, and the resistor 306. The electrical characteristics of the capacitor 302 and the resistor 306 are affected by the ambient temperature. For example, the resistance of the resistor 306 may be based on a temperature coefficient (e.g., temperature coefficient of resistance) of the resistor 306. Similar to and/or the same as the relationship of the temperature coefficient with the capacitor 304, changes in ambient temperature of the resistor 306 relative to a reference temperature adjusts the resistance defined by the temperature coefficient. In connection with FIG. 5, the electrical characteristics of the resistor 306 modifies the excitation signal 406 by generating a response 504 having an adjusted amplitude 502. For example, the electrical characteristics of the respiratory sensor 1110 represents an adjusted frequency and/or amplitude of the excitation signal 406

Figure 5:
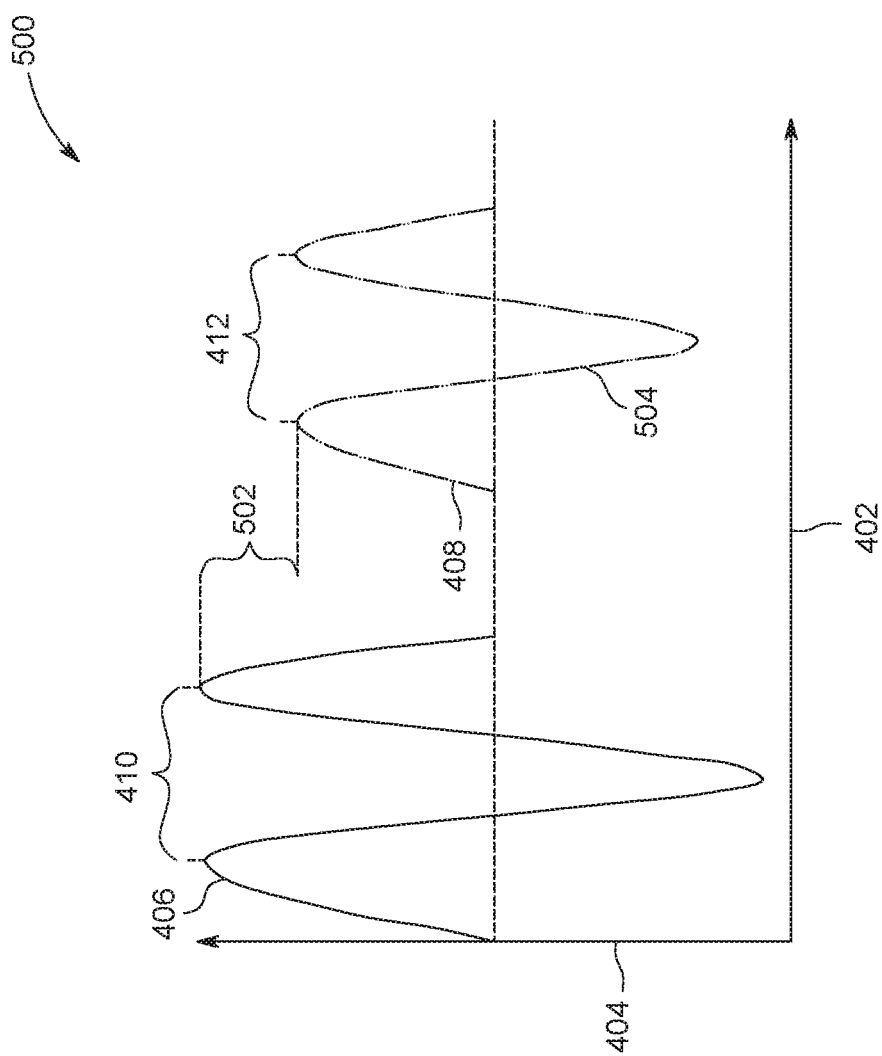
FIG. 5 is a graphical illustration of an excitation signal and a response, in accordance with an embodiment.

FIG. 5 is a graphical illustration 500 of the excitation signal 406 and the response 504, in accordance with an embodiment. The response 504 represents a modified reflection of the excitation signal 406 based on the electrical characteristics of the respiratory sensor 110, such as the capacitor 302 and the resistor 306. The controller circuit 102 is configured to analyze the response 408 to determine at least one of the temperature or flow rate of the airflow path based on the temperature coefficient of the capacitor 302. As described above in reference to FIG. 4, the controller circuit 102 may be configured to identify a change in frequency of the response signal 504 relative to the excitation signal 406. In another example, the controller circuit 102 may determine a change in amplitude 502 of the response 504 relative to the excitation signal 406. The change in amplitude 502 is based on the resistance of the resistor 306. Based on the change in amplitude, the controller circuit 102 may calculate the change in resistance of the resistor 306 relative to the resistance value stored in the memory 108. For example, the memory 108 may store the electrical characteristics of the inductor 304, the capacitor 302, the resistor 306, and the temperature coefficients of the resistor and capacitor. The controller circuit 102 may determine the temperature of the respiratory sensor 110 utilizing the adjusted resistance, which represents a temperature of the airflow path based on the temperature coefficient and the electrical characteristics of the respiratory sensor 110. Additionally or alternatively, the controller circuit 102 may compare the temperature value determined from the capacitance (e.g., change in frequency) and the resistance (e.g., change in amplitude). For example, the controller circuit 102 may calculate an average temperature value of the respiratory sensor 110 based on the temperature determinations from the change in frequency and change in amplitude.

It may be noted that the respiratory sensor 110 may have at least one of the capacitor 302, the inductor 304, and the resistor 306. In connection with FIG. 3C, the schematic diagram 360 illustrates the respiratory sensor 110 having the inductor 304 and the resistor 306. For example, the controller circuit 102 may determine the temperature and/or flow rate based on changes in the electrical characteristics, such as the change in amplitude of the response relative to the excitation signal.

Figure 6:
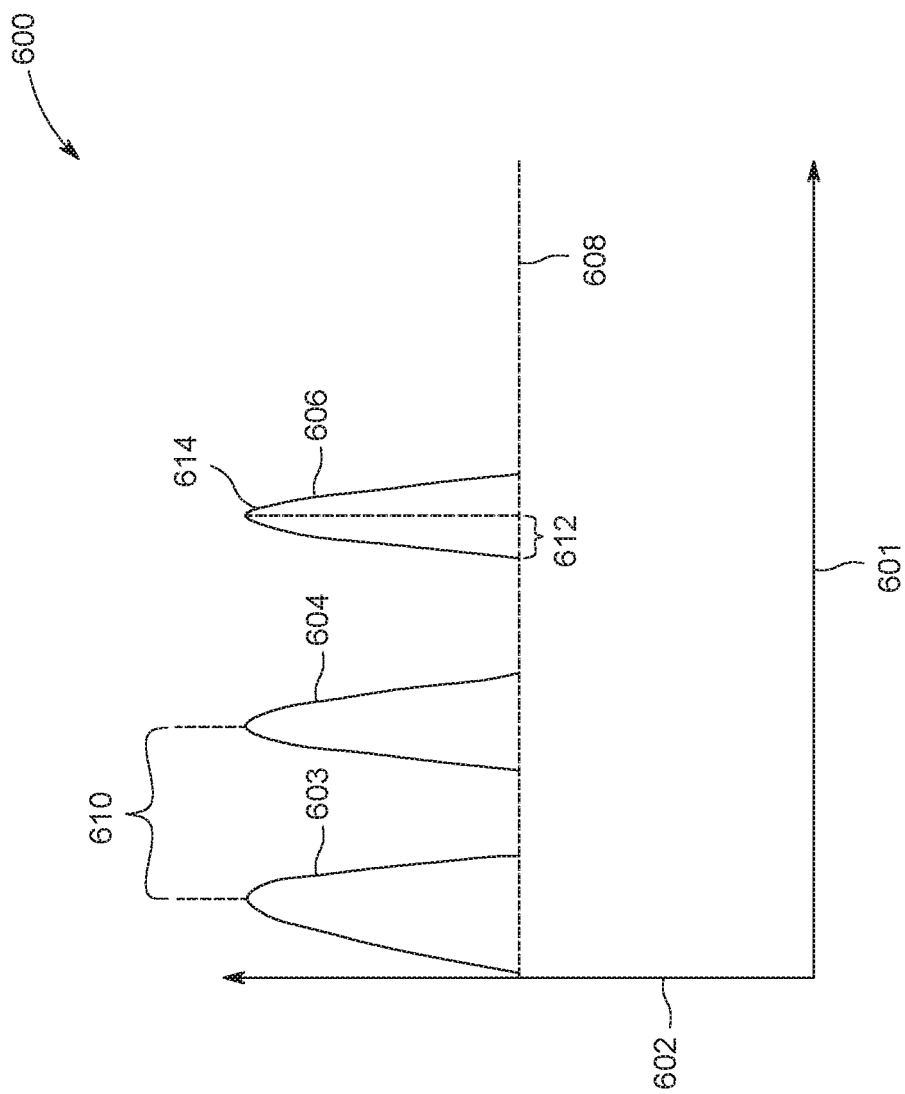
FIG. 6 is a graphical illustration of temperature changes of a respiratory sensor, in accordance with an embodiment.

In connection with FIG. 6, the controller circuit 102 may calculate a respiratory rate based on the temperature changes. FIG. 6 is a graphical illustration 600 of temperature changes of the respiratory sensor 110, in accordance with an embodiment. The temperature changes are plotted along a horizontal axis 601 representing time and a vertical axis 602 representing temperature. For example, the temperature changes are illustrated as temperature peaks 603-606. The peaks 603-606 may correspond to a series of temperature values determined by the controller circuit 102 based on the electrical characteristics of the respiratory sensor 110. For example, the excitation signal 406 may be continually and/or repeatedly transmitted by the transmission circuit 112 at a sample rate and/or set period of time. The controller circuit 102 may generate the excitation signal 406, which is transmitted by the transmission circuit 112, every 50 ms. Additionally or alternatively, the rate at which the excitation signal 406 is transmitted is based on a characteristic (e.g., age, weight, height) of the patient. For example, an infant may generally have a higher respiratory rate (e.g., 25-40 breaths per minute) than an adult (e.g., over 18 years old) patient (e.g., 12-18 breaths per minute). The controller circuit 102 may increase the sample rate of which the excitation signal 406 is transmitted by the transmission circuit 112 for an infant relative to an adult patient.

Based on the temperature peaks 603-606, the controller circuit 102 may determine a respiratory rate of the patient. For example, the temperature peaks 603-606 correspond to an increase in temperature corresponding to an inhalation of the ambient air of the airflow path into the body 202 of the patient relative to a room temperature 608. The controller circuit 102 is configured to identify the peaks 603-606, and based on a position of the peaks 603-606 relative to each other along the horizontal axis 601, representing time, determine the respiratory rate of the patient. For example, the controller circuit 102 may calculate a period 610 between temperature peaks 603-604 as 4 seconds representing a respiratory rate of 15 breaths per minute. Additionally or alternatively, the controller circuit 102 may calculate an average respiratory rate based on more than two peaks 603-606.

Optionally, the controller circuit 102 may determine a flow rate based on the electrical characteristics of the respiratory sensor 110. The flow rate of the ambient air along the airflow path corresponds to a rate of temperature change of the respiratory sensor 110. For example, the rate of temperature change may be based on a peak time 612. The peak time 612 may represent a length of time for the temperature of the respiratory sensor 110 to transition from a first temperature (e.g., the room temperature 608) to a second temperate (e.g., a peak temperature 614). A surface area of the respiratory sensor 110 within the airflow path may be stored in the memory 108. The surface area may represent a surface area of the capacitor 302 and/or the resistor 306. Based on a rate of temperature change and the surface area, the controller circuit 102 may determine a flow rate.

Figure 7:
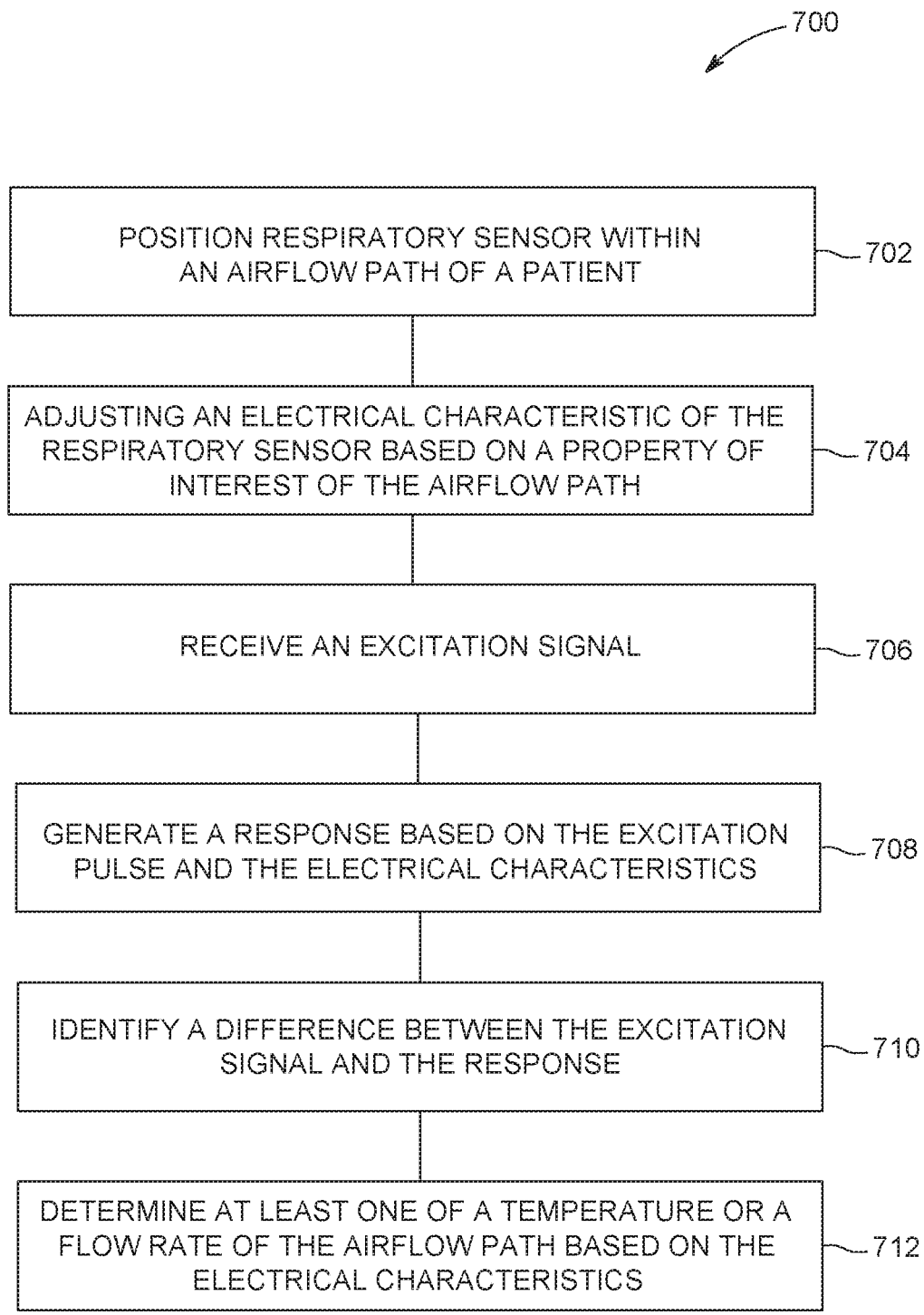
FIG. 7 is a flow chart of a method for respiratory monitoring of a patient, in accordance with an embodiment.

FIG. 7 is a flow chart of a method 700 for respiratory monitoring of a patient, in accordance with an embodiment. The method 700, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be used as one or more algorithms to direct hardware to perform one or more operations described herein.

Beginning at 702, the respiratory sensor 110 is configured to be positioned within an airflow path of a patient. For example in connection with FIGS. 2A-B, at least a portion of the respiratory sensor 110 may be positioned proximate to one or more nostrils 204, 206 of the patient. The position of the respiratory sensor 110 is such that at least one or more components (e.g., at least one of the capacitor, inductor, resistor) of the respiratory sensor 110 is exposed to changes in direction and/or speed of the ambient air based on a respiratory action (e.g., inhale, exhale) of the patient.

At 704, the respiratory sensor 110 is configured to adjust an electrical characteristic based on a property of interest of the airflow path. For example, the property of interest may correspond to a temperature or flow rate of the airflow path. As air along the airflow path is transitioned (e.g., inhaled, exhaled), a temperature of the components (e.g., capacitor 302, resistor 306) is changed. The electrical characteristics are adjusted corresponding to the temperature coefficients of the components of the respiratory sensor 110.

At 706, the respiratory sensor 110 is configured to receive the excitation signal 406. For example, the controller circuit 102 may generate the excitation signal 406 having predetermined electrical characteristics (e.g., frequency, amplitude). The excitation signal 406 may be transmitted by the transmission circuit 112. For example, the transmission circuit 112 may be capacitively coupled to the respiratory sensor 110, and communicate the excitation signal 406 utilizing a communication channel within the body. In another example, the transmission circuit 112 may include an RF circuit configured to transmit the excitation signal 406 using a magnetic field.

At 708, the respiratory sensor 110 is configured to generate a response (e.g., the response 408, 504) based on the excitation pulse and the electrical characteristics. For example, the respiratory sensor 110 may reflect the excitation pulse 406 to form the response. The electrical characteristics of the respiratory sensor 110 modifies and/or adjusts the excitation pulse 406 to form the response. For example, the frequency of the excitation pulse 406 may be adjusted based on the resonance frequency of the respiratory sensor 110. In another example, an amplitude of the excitation pulse 406 may be adjusted based on a resistance of the respiratory sensor 110.

At 710, the controller circuit 102 is configured to identify a difference between the excitation signal 406 and the response. For example, the controller circuit 102 may receive the response via the transmission circuit 112. The controller circuit 102 may compare the electrical characteristics of the excitation signal 406 (e.g., frequency, amplitude) to identify differences of the response relative to the excitation signal 406.

At 712, the controller circuit 102 is configured to determine at least one of a temperature or a flow rate of the airflow path based on the electrical characteristics. The electrical characteristics of the respiratory sensor 110 is represented by the difference between the excitation signal 406 and the response. For example, the controller circuit 102 may identify a frequency change of the response relative to the excitation signal 406. The controller circuit 102 may determine the capacitance based on the frequency of the response and compare the capacitance to the capacitance at a reference temperature stored in the memory 108. Based on the temperature coefficient of the capacitor 302, the controller circuit 102 can determine the temperature change corresponding to the change in capacitance to result in the electrical characteristics of the frequency of the respiratory sensor 110. In another, the controller circuit 102 may identify an amplitude change of the response relative to the excitation signal 406. The controller circuit 102 may determine the resistance based on the amplitude of the response and compare the resistance to the resistance at a reference temperature stored in the memory 108. Based on the temperature coefficient of the resistor 306, the controller circuit 102 can determine the temperature change corresponding to the change in resistance to result in the electrical characteristics of the amplitude of the respiratory sensor 110.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "circuit" or "module" may include a processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term computer," "subsystem," "circuit" or "module". The one or more processors execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A respiratory monitoring system comprising:
a respiratory sensor configured to be positioned within an airflow path of a patient;
a transmission circuit communicatively coupled to the respiratory sensor, wherein the transmission circuit is configured to transmit an excitation signal to the respiratory sensor, the respiratory sensor is configured to generate a response based on the excitation signal, and the response generated by the respiratory sensor is indicative of respiration of the patient, wherein the respiratory sensor includes a communication circuit configured to be communicatively coupled to the transmission circuit using a communication channel within a body of the patient, the communication circuit and the transmission circuit configured to be in contact with the body; and
a controller circuit operably coupled to the transmission circuit and configured to identify temperature peaks using the response generated by the respiratory sensor, and to determine a respiratory rate of the patient using the temperature peaks.

2. The respiratory monitoring system of claim 1, wherein the respiratory sensor has a resonant circuit that includes an inductor and a capacitor, the resonant circuit having a resonant frequency that varies based on a temperature of the airflow path, wherein the response generated by the respiratory sensor is based on both the excitation signal and the resonant frequency of the resonant circuit.

3. The respiratory monitoring system of claim 2, wherein the response generated by the respiratory sensor corresponds to the excitation signal modified by the resonant frequency.

4. The respiratory monitoring system of claim 2, wherein the controller circuit is configured to determine at least one of the temperature of the airflow path or a flow rate of the airflow path based on the resonant frequency.

5. The respiratory monitoring system of claim 4, wherein one or more of the inductor or the capacitor of the respiratory sensor has a predetermined temperature coefficient that represents the resonant frequency, wherein the controller circuit is configured to analyze the response generated by the respiratory sensor to determine the at least one of the temperature of the airflow path or the flow rate of the airflow path based on the predetermined temperature coefficient.

6. The respiratory monitoring system of claim 5, wherein the controller circuit is configured to identify a difference between the excitation signal and the response generated by the respiratory sensor to determine the at least one of the temperature of the airflow path or the flow rate of the airflow path based on the difference.

7. The respiratory monitoring system of claim 2, wherein the resonant frequency of the resonant circuit represents an adjusted frequency or amplitude of the excitation signal.

8. A method for respiratory monitoring of a patient, the method comprising:
positioning a transmission circuit, that generates an excitation signal, and a respiratory sensor in contact with a body of the patient, wherein the respiratory sensor is positioned within an airflow path of the patient, wherein the respiratory sensor includes a communication circuit communicatively coupled to the transmission circuit using a communication channel within the body of the patient;
receiving the excitation signal at the respiratory sensor;
generating a response of the respiratory sensor based on the excitation signal, wherein the response generated by the respiratory sensor is indicative of respiration of the patient;
identifying temperature peaks using the response generated by the respiratory sensor; and
determining a respiratory rate of the patient using the temperature peaks.

9. The method of claim 8, further comprising adjusting a resonant frequency of a resonant circuit in the respiratory sensor based on a temperature of an airflow path of the patient, the resonant circuit having an inductor and a capacitor, wherein the response of the respiratory sensor is generated based on both the excitation signal and the resonant frequency of the resonant circuit.

10. The method of claim 9, further comprising determining at least one of the temperature of the airflow path or a flow rate of the airflow path based on the resonant frequency.

11. The method of claim 10, further comprising identifying a difference between the excitation signal and the response of the respiratory sensor, wherein the at least one of the temperature of the airflow path or the flow rate of the airflow path is determined based on the difference between the excitation signal and the response of the respiratory sensor.

12. The method of claim 9, wherein the response of the respiratory sensor is generated by modifying the excitation signal based on the resonant frequency.

13. The method of claim 9, wherein at least one of the capacitor or the inductor of the resonant circuit in the respiratory sensor has a predetermined temperature coefficient that represents the resonant frequency.

14. The method of claim 9, wherein the resonant frequency represents an adjusted frequency or amplitude of the excitation signal.

15. A respiratory monitoring system comprising:
a respiratory sensor configured to be positioned within an airflow path of a patient and placed in contact with a body of the patient, the respiratory sensor having a resonant circuit with an inductor and a capacitor, the resonant circuit having a resonant frequency that varies based on a temperature of the airflow path;
a transmission circuit configured to be communicatively coupled to the respiratory sensor using a communication channel within the body of the patient, wherein the transmission circuit is configured to transmit an excitation signal to the respiratory sensor and the respiratory sensor is configured to generate a response based on the excitation signal and the resonant frequency; and
a controller circuit operably coupled to the transmission circuit, wherein the controller circuit is configured to identify temperature peaks based on the resonant frequency, and to determine a respiratory rate of the patient using the temperature peaks.

16. The respiratory monitoring system of claim 15, wherein at least one of the capacitor or the inductor of the resonant circuit of the respiratory sensor has a predetermined temperature coefficient that represents the resonant frequency, the controller circuit configured to analyze the response to determine at least one of the temperature of the airflow path or a flow rate of the airflow path based on the predetermined temperature coefficient.

17. The respiratory monitoring system of claim 15, wherein the controller circuit is configured to identify a difference between the excitation signal and the response to determine at least one of the temperature of the airflow path or a flow rate of the airflow path based on the difference.

\* \* \* \* \*